US012748048B2

(12) United States Patent
Zayats et al.

(10) Patent No.: US 12,748,048 B2
(45) Date of Patent: Sep. 29, 2026

(54) PLASMONIC HYDROGEN DETECTION

(71) Applicant: KING'S COLLEGE LONDON, London (GB)

(72) Inventors: Anatoly Zayats, London (GB); Wayne Dickson, London (GB); Mazhar Ejaz Nasir, London (GB)

(73) Assignee: KING'S COLLEGE LONDON, London (GB)

( * ) Notice: Subject to any disclaimer, the term of this patent is extended or adjusted under 35 U.S.C. 154(b) by 0 days.

(21) Appl. No.: 14/890,372

(22) PCT Filed: May 12, 2014

(86) PCT No.: PCT/GB2014/051448
§ 371 (c)(1),
(2) Date: Nov. 10, 2015

(87) PCT Pub. No.: WO2014/184530
PCT Pub. Date: Nov. 20, 2014

(65) Prior Publication Data

US 2016/0123878 A1 May 5, 2016

(30) Foreign Application Priority Data

May 13, 2013 (GB) ...................................... 1308515

(51) Int. Cl.
*G01N 21/552* (2014.01)
*G01N 21/77* (2006.01)
*G01N 33/00* (2006.01)

(52) U.S. Cl.
CPC ........... *G01N 21/554* (2013.01); *G01N 21/77* (2013.01); *G01N 33/005* (2013.01);
(Continued)

(58) Field of Classification Search
CPC ............. G01N 21/554; G01N 21/7703; G01N 33/055; G01N 21/77
See application file for complete search history.

(56) References Cited

U.S. PATENT DOCUMENTS 9,523,152 B2 * 12/2016 Chou .................... C23C 14/081

FOREIGN PATENT DOCUMENTS

DE 102011101698 A1 * 11/2012 ............. G01N 21/49
WO 2012/169971 A1 12/2012
WO 2014/162147 A1 10/2014

OTHER PUBLICATIONS

Jaksic, Zoran, Olga Jaksic, Zoran Djuric, Christoph Kment, "A consideration of the use of metamaterials for sensing applications: field fluctuations and ultimate performance," J. Opt. A: Pure Appl. Opt. 9 (2007) S377-S384.*

(Continued)

*Primary Examiner* — Rebecca C Bryant
(74) *Attorney, Agent, or Firm* — KENEALY VAIDYA LLP

(57) ABSTRACT

Some embodiments are directed to a plasmonic hydrogen detector and method of constructing a plasmonic hydrogen detector. The plasmonic hydrogen detector includes: a structure having a support and a plurality of nanostructure elements. The plurality of nanostructure elements include a plasmonic material and a hydrogen sensitive material. The plurality of nanostructure elements are configured on the support to allow the structure to act as a plasmonic metamaterial. The hydrogen sensitive material is configured to cause a change in permittivity of the plasmonic metamaterial in the presence of hydrogen. Aspects and embodiments described recognize that use of a plasmonic metamaterial as a hydrogen detector can result in a highly sensitive detector. That sensitivity stems from the sensitivity of strong plasmonic coupling between individual nanostructure elements (Continued)

Incident ⟶, reflected ⇢ and transmitted - - -▸ electromagnetic radiation.

in the metamaterial to external perturbations, for example, as a result of a physical or chemical environmental change.

17 Claims, 3 Drawing Sheets

(52) U.S. Cl.
CPC ................ *G01N 2021/7773* (2013.01); *G01N 2021/7783* (2013.01); *G01N 2201/06113* (2013.01); *G01N 2201/068* (2013.01)

(56) References Cited

OTHER PUBLICATIONS

Kravets, V.G., Schedin, Jalil, Britnell, Gorbachev, Ansell, Thackray, Novoselov, Geim, Kabashin, Grigorenko, "Singular phase nano-optics in plasmonic metamaterials for label free single molecule detection," Nature Materials, vol. 12, Apr. 2013, pp. 304-309.*
Christ A, Tikhodeev SG, Gippius NA, Kuhl J, Giessen H. Waveguide-plasmon polaritons: strong coupling of photonic and electronic resonances in a metallic photonic crystal slab. Phys Rev Lett. Oct. 31, 2003;91(18):183901. doi: 10.1103/PhysRevLett.91.183901. Epub Oct. 28, 2003. PMID: 14611284.*
D. Nau, A. Seidel, R. B. Orzekowsky, S.-H. Lee, S. Deb, and H. Giessen, "Hydrogen sensor based on metallic photonic crystal slabs," Opt. Lett. 35, 3150-3152 (2010).*
Martinez, Alejandro. Plasmonic metamaterials. Keesing Platform, https://platform.keesingtechnologies.com/plasmonic-metamaterials/. Jan. 10, 2015.*
Jul. 15, 2014 International Search Report and Written Opinion of the International Searching Authority issued in International Application No. PCT/GB2014/051448.
Andreas Tittl et al., "Palladium-Based Plasmonic Perfect Absorber in the Visible Wavelength Range and Its Application to Hydrogen Sensing," Nano Letters, vol. 11, No. 10, Aug. 30, 2011, pp. 4366-4369.
Maeda E. et al., "Array of subwavelength rectangular structures in palladium for optical hydrogen detection," Proceedings of SPIE, vol. 8264, Feb. 9, 2012, pp. 82640N-1-82640N-5.
Nasir M. E. et al., "Hydrogen Detected by the Naked Eye: Optical Hydrogen Gas Sensors Based on Core/Shell Plasmonic Nanorod Metamaterials," Advanced Materials, vol. 26, No. 21, Mar. 18, 2014, pp. 3532-3537.
A. V. Kabashin et al., "Plasmonic nanorod metamaterials for biosensing," Nature Materials, vol. 8, No. 11, Oct. 11, 2009, pp. 867-871.

* cited by examiner

Incident ⟶, reflected ⇢ and transmitted - - -⇢ electromagnetic radiation.

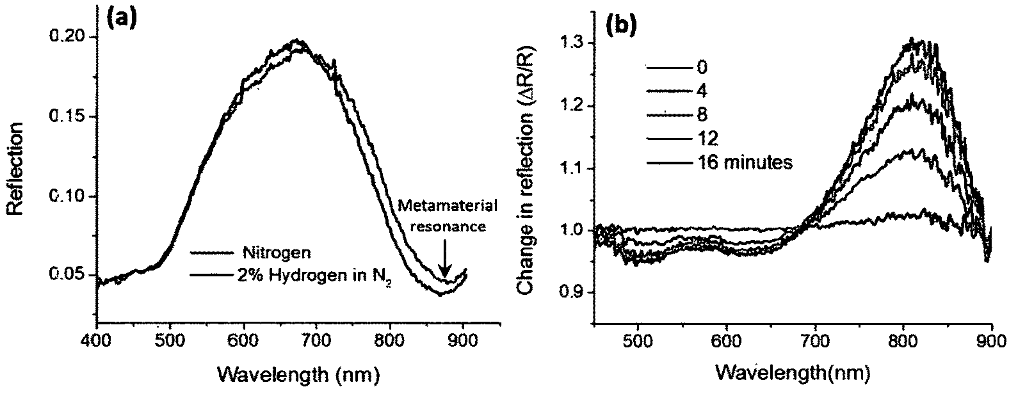

Figure 3: Optical Metamaterial based hydrogen sensing. (a) Reflection at an angle of 50 degrees and (b) Change in reflection as a function of wavelength for different durations of exposure to 2% Hydrogen in Nitrogen

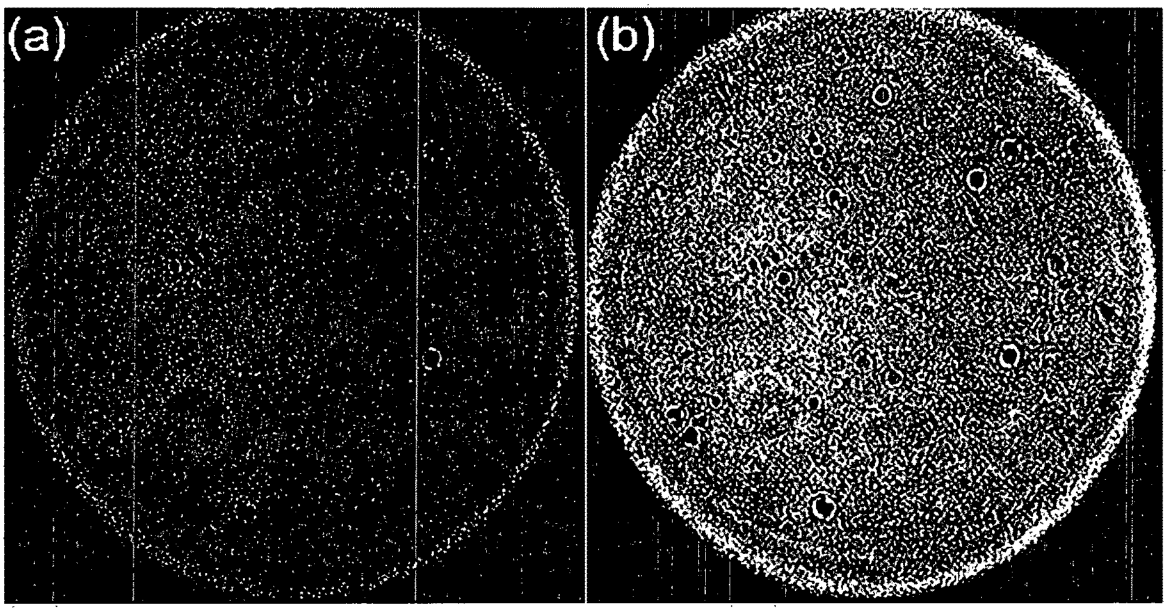

Figure 4: The visual response of the sensor. Optical image in the presence of (a) Nitrogen/Air exhibiting low reflectivity and (b) obvious brightening in the presence of 2% Hydrogen in Nitrogen.

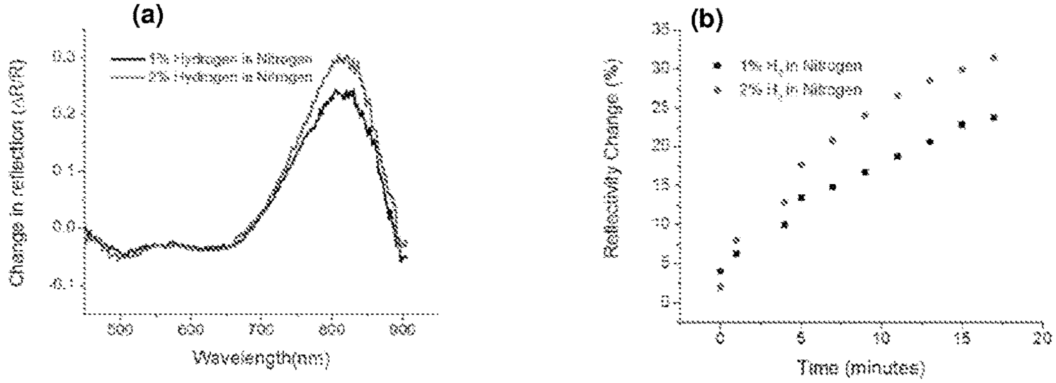
Figure 5: Performance of the sensor in different $H_2$ concentrations. (a) Change in reflection on exposure to 1% and 2% $H_2$ in Nitrogen and (b) Reflectivity change with time at a wavelength of 820 nm in different concentrations of hydrogen.
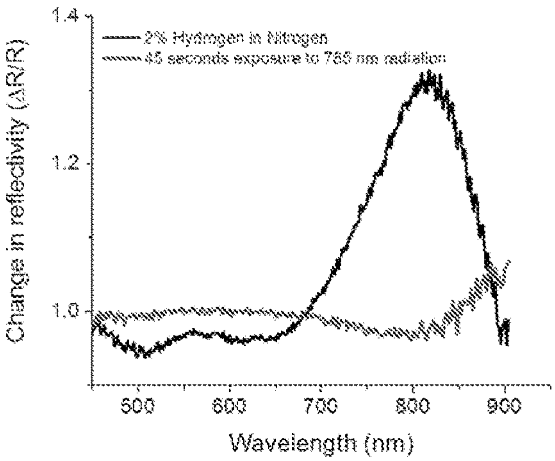
Figure 6: Reversibility on application of laser radiation at 785 nm. The return to the baseline is completely recovered after exposure.

PLASMONIC HYDROGEN DETECTION

CROSS REFERENCE TO RELATED APPLICATION

This application is a National Phase filing under 35 C.F.R. § 371 of and claims priority to PCT Patent Application No.: PCT/GB2014/051448, filed on May 12, 2014, which claims the priority benefit under 35 U.S.C. § 119 of British Application No.: 1308515.4, filed on May 13, 2013, the contents of which are hereby incorporated in their entireties by reference.

FIELD OF THE INVENTION

Aspects provide a plasmonic hydrogen detector and method of constructing a plasmonic hydrogen detector. There is also provided a method of detecting a change in hydrogen concentration in an environment using a plasmonic hydrogen detector in accordance with described aspects and apparatus operable to perform that method.

BACKGROUND

Hydrogen is a widely used, but highly explosive, gas which requires only a very low concentration for combustion. Due to safety concerns and public perceptions about hydrogen, one issue of relevance is development of a reliable hydrogen detection technique. It will be appreciated that hydrogen is a gas widely used in petrochemical processing, hydrogen refuelling stations, nuclear power plants and fuel cell manufacturing. In such environments the detection of hydrogen can be an important safety concern.

Conventionally used hydrogen detection means are typically of a semiconductor type, or employ protonic conductors or simple platinum wires. Such sensors usually require electrical readings and the sensitivity of those sensors is typically enhanced at a high working temperature which can be undesirable given the explosive nature of hydrogen.

Several approaches to detecting hydrogen by using an all-optical sensor have been studied, but such approaches appear not to be able to offer a sensitive means of detection.

It is desired to provide an alternative means of hydrogen detection which addresses some of the issues with existing hydrogen detectors.

SUMMARY

Accordingly, a first aspect provides a plasmonic hydrogen detector comprising: a structure comprising a support and a plurality of nanostructure elements comprising a plasmonic material and a hydrogen sensitive material; the plurality of nanostructure elements being configured on the support to allow the structure to act as a plasmonic metamaterial; and wherein the hydrogen sensitive material is configured to cause a change in permittivity of the plasmonic metamaterial in the presence of hydrogen.

Aspects and embodiments described recognise that use of a plasmonic metamaterial as a hydrogen detector can result in a highly sensitive detector. That sensitivity stems from the sensitivity of strong plasmonic coupling between individual nanostructure elements in the metamaterial to external perturbations, for example, as a result of a physical or chemical environmental change. Provision of a hydrogen sensitive material as an element within said metamaterial causes a change to said metamaterial in the presence of hydrogen. That change, in this instance, a change to the effective permittivity of the metamaterial can be detected by various appropriately chosen techniques.

Although it is possible to construct various hybrid hydrogen sensitive material based plasmonic systems for detection of hydrogen, for example, palladium-based plasmonic systems, such hybrid plasmonic systems are based on localised plasmon resonance sensing or surface plasmon polaritonic structures. Such systems may, for example, comprise a film or layer or a plasmonic material, onto which a film or layer of hydrogen sensitive material is placed. In some cases, the hydrogen sensitive layer, for example, palladium, may be arranged on said plasmonic material in a structured manner, for example, a grating, thus requiring sophisticated optical interrogation techniques to be used to detect hydrogen. Such structures typically require expensive lithographic fabrication techniques which makes them expensive and technologically challenging to fabricate.

Aspects and embodiments described herein recognise that the optical properties of plasmonic systems and metamaterials based on the arrangement of plasmonic components present an opportunity to design novel optical devices which may offer useful properties. Electromagnetic metamaterials can exhibit high sensitivity to their surroundings and thus can offer a means to create a sensitive detector.

Use of a plasmonic metamaterial which is sensitive to hydrogen may allow aspects and embodiments to provide a rapid, sensitive and accurate hydrogen detector. Depending upon the precise configuration of the nanostructured elements forming the metamaterial, hydrogen may be detected at low concentrations and thus a detector based upon such a metamaterial may provide a means to limit potential hazards associated with the use of the highly explosive hydrogen gas. Some aspects and embodiments may provide a hydrogen sensor which can operate to safely detect hydrogen gas at room temperature.

In one embodiment, the plasmonic metamaterial comprises an electromagnetic metamaterial. It will be appreciated that excitation of a plasmon may be achieved by means of appropriate radiation. Furthermore, it will be appreciated that a change to the hydrogen sensitive material can result in change in the optical properties of the metamaterial and therefore a change to reflection or transmission properties of the metamaterial may occur even off-resonance. In one embodiment, the plasmonic metamaterial comprises an optical metamaterial. Accordingly, providing incident energy in the form of, for example, photons may excite surface plasmons. Whether a nanostructure is seen by interrogating incident radiation as a metamaterial is likely to depend upon the relative wavelength of the incident radiation in comparison to the spacing of adjacent nanostructure elements. In particular, it will be appreciated that for a given wavelength of interrogating incident electromagnetic radiation, the spacing of adjacent nanostructure elements may be in the region of a few tens of nanometres to several microns.

In one embodiment, adjacent nanostructure elements are configured on the support such that they are electromagnetically coupled. In one embodiment, the nanostructure elements are configured such that the electromagnetic field of one nanostructure element spatially overlaps that of adjacent nanostructure elements. Accordingly, rather than being seen by incident radiation as separate component elements, the nanostructure acts as a metamaterial. Arranging adjacent elements to display strong near-field interaction may ensure that the resultant structure acts as a metamaterial.

In one embodiment, the plurality of nanostructure elements are configured as an array on the support. Accordingly, that array may comprise a regular array or grid. In some embodiments, that array may comprise a quasi-regular array, such as a forest. Such a quasi-regular structure may result from structures being grown on, for example, a porous dielectric template. The pores of such a template may be located substantially regularly, as a result of employing a multi-step anodisation process. In one embodiment, the array comprises a substantially regular array.

In one embodiment, the adjacent nanostructure elements have a spacing of the order of a few tens of nanometres to several microns, that spacing being determined by the wavelength of electromagnetic radiation selected to be incident on a resulting metamaterial. The spacing can be selected such that it is typically smaller than, but not limited to, the effective wavelength of intended interrogating radiation inside the metamaterial.

In one embodiment, the plurality of nanostructure elements are configured to provide a sub-set of nanostructure elements formed from hydrogen sensitive material interspersed amongst the plurality of nanostructure elements comprising a plasmonic material. Accordingly, entire nanostructure elements may be formed from a plasmonic material and entire nanostructure elements may be formed from a hydrogen sensitive material. The metamaterial may be configured so that those entire nanostructure elements formed from a hydrogen sensitive material are interspersed with those entire nanostructure elements formed from a plasmonic material. The relative number of hydrogen sensitive elements may be selected such that the nanostructure elements formed from a plasmonic material allow for the resulting metamaterial to exhibit plasmonic characteristics. That is to say, the concentration of hydrogen sensitive elements within the metamaterial may not be so high as to destroy overlap of electromagnetic field between adjacent plasmonic nanostructures. Nonetheless, the concentration must be selected to be sufficient to allow a resulting metamaterial to exhibit a change in permittivity in the presence of hydrogen.

In one embodiment, each of the nanostructure elements comprises: a plasmonic material and a hydrogen sensitive material. Accordingly, in some embodiments, a plurality of nanostructure elements comprise both a plasmonic material and a hydrogen sensitive material. Such an arrangement may allow for a highly hydrogen sensitive metamaterial, since an external perturbation, such as the presence of hydrogen, causes a change to the underlying metamaterial structure, and/or optical properties via a modification of the material's permittivity, as a result of the reaction of the hydrogen sensitive material forming the nanostructure elements to the presence of hydrogen.

It will be appreciated that various nanostructure elements may be used to form an appropriate metamaterial. In one embodiment, the nanostructure elements comprise a plasmonic material core. In one embodiment, the plasmonic material core comprises a hollow structure. That hollow structure may, for example, comprise a hollow tube. In one embodiment, the nanostructure elements comprise elongate elements extending from the support. In one embodiment, the nanostructure elements comprise a plasmonic material core having a hydrogen sensitive material coating. In one embodiment, the coating comprises a complete coating. In some embodiments, the coating may comprise a partial coating. In some embodiments only a proportion of said plasmonic material cores are coated in said hydrogen sensitive material. In one embodiment, the coating has a thickness a fraction of a nanometre to several hundred nanometres, that coating thickness being selected such that the thickness of the coating is less than half the spacing between individual plasmonic elements forming the metamaterial. The thickness of the coating may be chosen with desired detector sensitivity and response time in mind. Too little hydrogen sensitive material may limit the impact of hydrogen in an environment, meaning that the detector does not respond significantly to the presence of hydrogen. If the coating is, however, too thick, the response of the material in the presence of hydrogen may also be limited, the absorption of hydrogen, for example, may be limited by diffusion into the hydrogen sensitive coating.

In some embodiments, one or more of the nanostructure elements may themselves be layered. That is to say, one or more layers of hydrogen sensitive material may be interspersed with one or more layers of plasmonic material. Those layers may be of equal thickness, and/or may be configured to achieve a desired detector sensitivity.

In one embodiment, the plasmonic material comprises at least one of: copper, gold, silver or aluminium or a plasmonic doped semiconductor.

In one embodiment, the hydrogen sensitive material comprises a hydrogen absorptive material. In one embodiment, the hydrogen absorptive material comprises palladium. In one embodiment, the hydrogen absorptive material comprises a palladium nickel composite.

In one embodiment, the plasmonic metamaterial is configured to act as a bulk plasmonic waveguide. Accordingly, the resultant sensor may offer a quantitative indication of a detected concentration of hydrogen, since the sensitivity of a metamaterial acting as a waveguide may be greater than an arrangement in which only localised surface plasmons or surface plasmon polaritons are excited by incident interrogating radiation.

It will be appreciated that the plasmonic hydrogen detector according to the first aspect may be commissioned for use in a variety of detection arrangements. It may, for example, simply be located such that it is visible to the naked eye and a change in reflectivity may be detected by the human eye. That change in reflectivity, for example, an increase in reflectivity, may indicate the presence of hydrogen in an environment surrounding the plasmonic hydrogen detector. Other, more sensitive, detection arrangements may be used. In one embodiment, the plasmonic hydrogen detector further comprises a sensor operable to detect the change in permittivity of the plasmonic metamaterial in the presence of hydrogen. In one embodiment, the detector comprises one or more of: a photo diode, a ccd, a video camera, an analogue or digital camera, an optical-electrical transducer, photomultiplier or similar. In one embodiment, the detector is operable to monitor intensity of reflected or transmitted radiation incident upon the sensor.

A second aspect provides a method of forming a plasmonic hydrogen detector comprising a structure comprising a support and a plurality of nanostructure elements comprising a plasmonic material and a hydrogen sensitive material; the method of forming comprising: configuring the plurality of nanostructure elements on the support to allow the structure to act as a plasmonic metamaterial; and configuring the hydrogen sensitive material to cause a change in permittivity of the plasmonic metamaterial in the presence of hydrogen.

Various methods to form plasmonic metamaterials may be employed. According to one embodiment, an electrochemical fabrication method may be used. Such electrochemical fabrication methods may offer a cheap and simple means to create an appropriate plurality of nanostructure elements having an appropriate configuration to be used as a plasmonic metamaterial exhibiting sensitivity to hydrogen. In one embodiment, the method of configuring the plurality of nanostructure elements on the support comprises at least one anodisation step. In one embodiment, the method of configuring the plurality of nanostructure elements on the support comprises at least one electro-deposition step. In one embodiment, the method of configuring the plurality of nanostructure elements on the support comprises at least one etching step.

In one embodiment, the plasmonic metamaterial is configured to be an electromagnetic metamaterial.

In one embodiment, the plasmonic metamaterial is configured to be an optical metamaterial.

In one embodiment, the method comprises: configuring adjacent nanostructure elements on the support such that they are electromagnetically coupled.

In one embodiment, the method comprises: configuring nanostructure elements such that the electromagnetic field of one nanostructure element spatially overlaps that of adjacent nanostructure elements.

In one embodiment, the method comprises: configuring the plurality of nanostructure elements as an array on the support.

In one embodiment, the array comprises a substantially regular array.

In one embodiment, the adjacent nanostructure elements have a spacing of the order a few tens of nanometres to several microns, that spacing being determined by the wavelength of incident electromagnetic radiation used to interrogate the metamaterial detector. The spacing of adjacent nanostructure elements may be selected such that the spacing is typically smaller than, but not limited to, the effective wavelength of the intended interrogating radiation inside the resultant metamaterial.

In one embodiment, the method comprises: configuring the plurality of nanostructure elements to provide a sub-set of nanostructure elements formed from hydrogen sensitive material interspersed amongst the plurality of nanostructure elements comprising a plasmonic material.

In one embodiment, the method comprises: configuring each of the nanostructure elements from a plasmonic material and a hydrogen sensitive material.

In one embodiment, the nanostructure elements comprise a plasmonic material core.

In one embodiment, the plasmonic material core comprises a hollow structure.

In one embodiment, the nanostructure elements comprise elongate elements extending from the support.

In one embodiment, the method comprises: coating the nanostructure elements comprising a plasmonic material core with a hydrogen sensitive material.

In one embodiment, the coating comprises a complete coating.

In one embodiment, the coating has a thickness between, for example, a fraction of a nanometre to several hundred nanometres. The coating thickness may be selected based on a desired detector sensitivity. The coating thickness may be selected such that the thickness of the coating is less than half the spacing between adjacent plasmonic nanostructure elements forming the metamaterial.

In one embodiment, the plasmonic material comprises at least one of: copper, gold, silver or aluminium or a plasmonic doped semiconductor.

In one embodiment, the hydrogen sensitive material comprises a hydrogen absorptive material.

In one embodiment, the hydrogen absorptive material comprises palladium.

In one embodiment, the plasmonic metamaterial is configured to act as a bulk plasmonic waveguide.

In one embodiment, the method further comprises providing a detector operable to detect the change in permittivity of the plasmonic metamaterial in the presence of hydrogen In one embodiment, the detector comprises one or more of: a photo diode, a ccd, a video camera, an analogue or digital camera, an optical-electrical transducer, photomultiplier or similar.

In one embodiment, the method comprises arranging the detector to monitor intensity of reflected or transmitted radiation incident upon the sensor.

A third aspect provides a method of detecting a change in hydrogen concentration in an environment, the method comprising: providing a plasmonic hydrogen detector in accordance with the first aspect; arranging a source of electromagnetic radiation to be incident upon the plasmonic hydrogen detector; and monitoring the effect of the plasmonic hydrogen detector upon the incident electromagnetic radiation.

A fourth aspect provides apparatus operable to detect a change in hydrogen concentration in an environment, the apparatus comprising: a plasmonic hydrogen detector in accordance with the first aspect; a source of electromagnetic radiation arranged to be incident upon the plasmonic hydrogen detector; and an electromagnetic radiation monitor operable to monitor the effect of the plasmonic hydrogen detector upon the incident electromagnetic radiation.

Further aspects provide: a plasmonic target-substance detector comprising:

a structure comprising a support and a plurality of nanostructure elements comprising a plasmonic material and a target-substance sensitive material; the plurality of nanostructure elements being configured on the support such that adjacent nanostructure elements are electromagnetically coupled to allow the structure to act as a plasmonic metamaterial; and wherein the target-substance sensitive material is configured to cause a change in permittivity of the plasmonic metamaterial in the presence of the target-substance.

Aspects and embodiments described recognise that use of a plasmonic metamaterial as a substance detector can result in a highly sensitive detector. That sensitivity stems from the sensitivity of strong plasmonic coupling between individual nanostructure elements in the metamaterial to external perturbations, for example, as a result of a physical or chemical environmental change. Provision of a target-substance sensitive material as an element within said metamaterial causes a change to said metamaterial in the presence of the target substance. That change, in this instance, a change to the effective permittivity of the metamaterial can be detected by various appropriately chosen techniques.

According to some embodiments, the target-substance may comprise a fluid. That fluid may comprise a gas or a liquid. Such a detector may allow detection of a target substance as it flows around the nanostructure elements of the detector.

In one embodiment, the target substance may comprise a non-inert fluid. In one embodiment, the target substance may comprise a reactive fluid. In one embodiment, the target-substance sensitive material may comprise a material arranged to react with said target-substance.

In one embodiment, the target substance comprises ammonia. In one embodiment, the target-substance sensitive material comprises: an appropriately selected conducting polymer. Such a conducting polymer may, for example, comprise: polypyrrole (PPy). Polypyrrole becomes sensitive to the presence of selected gases if an appropriate functional dye is incorporates within the polymer. By way of example: for the purposes of ammonia detection, incorporation of eriochrome cyanine R (ECR) in PPy shows large changes in optical spectra via a variation of the complex refractive index when exposed to ammonia in the gas phase.

It will thus be appreciated that the apparatus and method of metamaterial enhanced detection described above and in the attached claims in relation to hydrogen detection may also be applied to detection of other materials, for example fluids, liquids or gases.

According to such alternative arrangements, a plasmonic metamaterial is formed or "hybridised" such that a plurality of nanostructure elements are provided comprising a plasmonic material and a target-substance sensitive material. The target-substance sensitive material may comprise an appropriately selected gas-sensitive material.

Further particular and preferred aspects are set out in the accompanying independent and dependent claims. Features of the dependent claims may be combined with features of the independent claims as appropriate, and in combinations other than those explicitly set out in the claims. Features of the variously described embodiments may be combined with features of various aspects as appropriate, and in combinations other than those explicitly set out above. In particular, one aspect may provide a method of forming a plasmonic target-substance detector analogous to the method of forming a plasmonic hydrogen detector described above. Furthermore, one aspect provides a method of detecting a change in target substance concentration in an environment and apparatus operable to detect a change in target substance concentration in an environment analogous to the method of detecting a change in hydrogen concentration in an environment and apparatus operable to detect a change in hydrogen concentration in an environment described above.

Where an apparatus feature is described as being operable to provide a function, it will be appreciated that this includes an apparatus feature which provides that function or which is adapted or configured to provide that function.

BRIEF DESCRIPTION OF THE DRAWINGS

Embodiments of the present invention will now be described further, with reference to the accompanying drawings, in which:

FIGS. 3*a* and 3*b* illustrate changes to electromagnetic radiation incident on a plasmonic metamaterial for use in some embodiments;

FIGS. 4*a* and 4*b* show a visual change to a sensor in the presence of hydrogen according to one embodiment;

FIGS. 5*a* and 5*b* illustrate performance of a sensor according to one embodiment in different hydrogen concentrations; and FIG. 6 illustrates the response to laser radiation of a plasmonic metamaterial for use in some embodiments.

DESCRIPTION OF THE EMBODIMENTS

Aspects and embodiments described herein may provide a plasmonic hydrogen detector. That plasmonic hydrogen detector is constructed from a plasmonic metamaterial. The plasmonic metamaterial itself comprises a support and a plurality of nanostructure elements. Those nanostructure elements comprise a plasmonic material and a hydrogen-sensitive material and are configured on the support to allow the structure to act as a plasmonic metamaterial. In particular, the hydrogen-sensitive material is arranged as part of the nanostructure elements forming the plasmonic material such that the presence of the hydrogen-sensitive material causes a change in permittivity of the plasmonic metamaterial resulting from the nanostructure in the presence of hydrogen.

Although it will be appreciated that an appropriate plasmonic metamaterial may be constructed in various ways, FIGS. 1*a* to 1*d* illustrate schematically main fabrication steps of a plasmonic metamaterial suitable for use in some embodiments of a detector.

According to one embodiment, a metamaterial can be based upon a self-assembled array of plasmonic particles each coated with a shell of hydrogen-sensitive material. One such hydrogen-sensitive material comprises palladium. Fabrication of one suitable metamaterial begins with the creation of an anodic aluminium oxide (AAO) template. That template is formed by means of anodisation of a substrate-supported aluminium thin film in, for example, sulphuric, phosphoric, or oxalic acid or any appropriate combination thereof. Such a template is shown schematically in FIG. 1*a*. The template shown in FIG. 1*a* comprises a glass layer too on which a thin film of gold 110 is provided and a layer of porous alumina 120.

Figure 1:
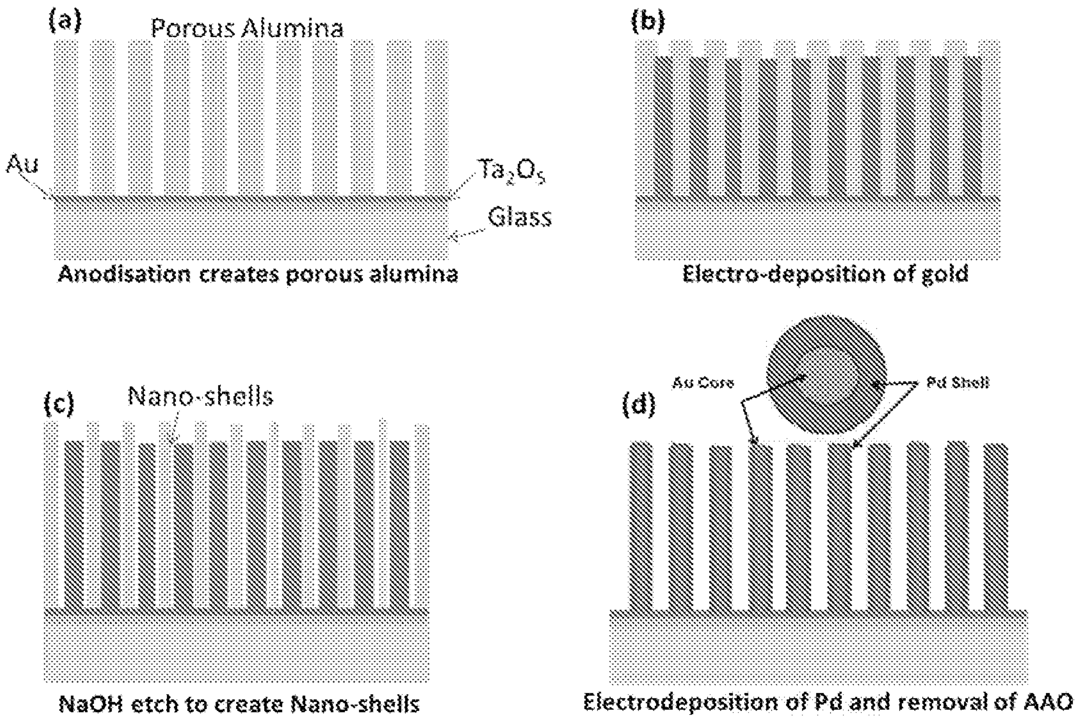
FIGS. 1*a* to 1*d* illustrate schematically main fabrication steps of a plasmonic metamaterial for use in some embodiments.

After anodisation, an array of plasmonic nanoparticles is electrodeposited into pores in the anodic aluminium oxide template. The electro deposition of gold is illustrated schematically in FIG. 1*b*. As shown in FIG. 1*b*, the pores in the anodic aluminium oxide template 120 are substantially filled by electrodeposited gold 130. After the electro deposition step, a nanometric airshell is etched around each gold nanorod 130. That nanometric airshell is formed by exposing the anodic aluminium oxide template to dilute (30 mM) NaOH. The airshell thickness determines the final palladium shelf thickness and is determined by controlling etch time. The airshells 140 formed around the gold nanorods 130 are shown schematically in FIG. 1*c*.

After forming a nanometric airshell, a hydrogen-sensitive shell material, in this example palladium, is grown around the gold nanorods 130 by means of electrodeposition into the shell of the anodic aluminium oxide template. A final fabrication step comprises removal of the anodic aluminium oxide matrix. That removal may occur by means of etching in NaOH. FIG. 1*d* illustrates schematically a possible plasmonic metamaterial structure which can result from the fabrication method described. As shown in FIG. 1*d*, gold nanorods 130 are coated with a palladium shell iso.

It will be appreciated that, at each stage of the fabrication process described, it is possible to take steps which will have an impact upon the final form of the resulting metamaterial. For example, as described above, the etch time determines the dimension of the nanometric airshell 140 formed around gold nanorods 130. Similarly, the precise dimensions of gold nanorods 130 may be determined by electro deposition techniques employed in the second fabrication step. It will be appreciated that it is possible to create a shell surrounding a nanorod made of sacrificial material (for example, polypyrrole) to create similar plasmonic tubes. Returning then to the fabrication steps described above, such plasmonic tubes may be coated in a hydrogen-sensitive material—for example, palladium.

It will be appreciated that precise dimensions of the metamaterial formed by such a fabrication method, and in particular the dimension of the metamaterial nanostructure elements, may depend upon the particular materials employed. In the example given above, the plasmonic material chosen is gold. It will be appreciated that alternative plasmonic materials may be chosen; for example, copper, silver, aluminium or an appropriately chosen plasmonic doped semiconductor. Similarly, the hydrogen-sensitive material chosen in the example above is palladium. To a certain extent, the plasmonic material chosen for construction of a suitable plasmonic metamaterial for use in some detector embodiments is likely to determine, to a certain extent, the wavelength of operation of a hydrogen detector. That is to say, the nanostructure elements forming the plasmonic metamaterial must be configured such that they exhibit plasmon resonance at the wavelength of operation and the nanostructure elements must have a separation which is small enough that there is spatial overlap of the electric field of one nanostructure element with its adjacent, or nearest, neighbours. Provided that condition is met, incident radiation is likely to see the structure as one material rather than the component nanostructure elements. In other words, the configuration of the nanostructure elements is such that a plasmonic metamaterial is formed.

After creation of a suitable plasmonic metamaterial from appropriately configured nanostructure elements, the metamaterial is adapted such that it exhibits a change in the presence of hydrogen. In particular, a metamaterial suitable for use in some embodiments is such that a hydrogen-sensitive material is arranged within the metamaterial to cause a change in permittivity of the plasmonic metamaterial in the presence of hydrogen.

In the fabrication method described above, the nanostructure elements are coated with palladium, a hydrogen-sensitive material. The high sensitivity of a device constructed using a plasmonic material such as that described above stems from a combination of the sensitivity of each individual nanostructure element and the near field interaction between adjacent nanostructure elements. That sensitivity means that changes to the size or shape of the nanostructure elements which may be caused by stress caused as a result of a change to the hydrogen-sensitive material in relation to the presence of hydrogen causes a change, in this case, to the metamaterial complex dielectric permittivity. The physical change to the nanostructure elements may result from stress, strain, bending moment or a combination of those factors is induced as a result of a change to the hydrogen-sensitive material forming part of the metamaterial in the presence of hydrogen.

Figure 2:
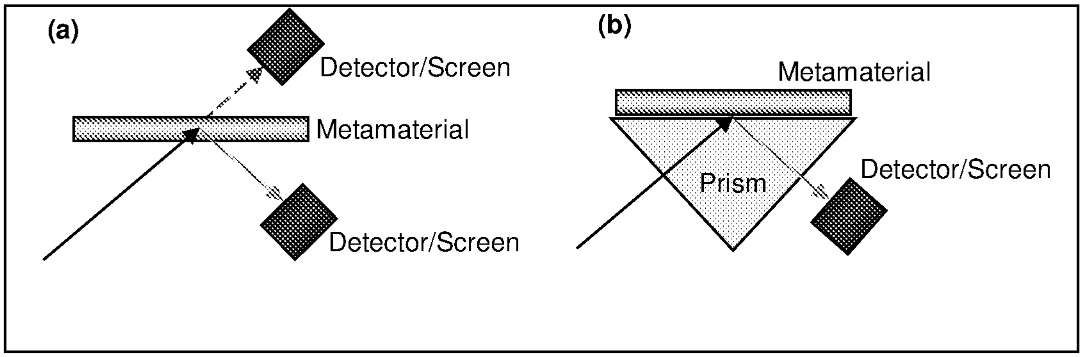
FIGS. 2*a* and 2*b* illustrate schematically a detection arrangement according to some embodiments.

FIG. 2*b* illustrates schematically detection arrangements according to some embodiments. In order to use a metamaterial (for example, one constructed in accordance with FIGS. 1*a* to 1*d*) as a hydrogen detector, a particular arrangement of components may be required. Two possible detection arrangements are shown in FIG. 2. A hydrogen-sensitive plasmonic metamaterial constructed to perform as a hydrogen detector is provided. That metamaterial 200 is subjected to incident radiation 210. Reflected radiation 220 and/or transmitted electromagnetic radiation 230 may be monitored by an appropriately selected detector 240. If hydrogen is present in the environment surrounding metamaterial 200 a change of properties of reflected and/or transmitted radiation may be detected by the appropriate detectors 240. In some embodiments the detector may comprise the naked eye. That is to say, in some embodiments the metamaterial may exhibit a physical change in the presence of hydrogen.

A device in accordance with aspects and embodiments may be used in either configuration shown in FIG. 2. In other words, the device may be used, for example, in transmission, reflection, or in attenuated total internal reflection arrangements as shown. Appropriate radiation sources and detectors for a particular wavelength or range of wavelengths of probing electromagnetic radiation may be used. In one particular arrangement developed to test the efficiency and sensitivity of an example metamaterial, the metamaterial was enclosed in a hydrogen cell.

Empirical Testing of Example Metamaterial

Tests have been carried out using an attenuated total internal reflection detection arrangement as shown in FIG. 2*b*. The test measurements were performed using a metamaterial in which the hydrogen-sensitive material was palladium and the plasmonic material comprised gold nanorods. Such a metamaterial was fabricated on a glass substrate and mounted onto a triangular prism using an appropriately chosen refractive index-matched solution. In this particular instance, the appropriate refractive index-matched solution comprised glycerol. The test metamaterial was illuminated at an angle above the angle of total internal reflection ($\theta_{ine}>\theta_e>44$ degrees), thereby facilitating excitation of bulk plasmonic waveguided modes in the nanorod layer of the metamaterial. Tests demonstrated that when hydrogen was absorbed by palladium in the metamaterial there was an accompanying expansion in lattice constant of the metamaterial. In other words, the metamaterial experienced volume expansion. When the palladium reacted chemically to form palladium hydride, the chemical reaction was accompanied by a shift of the Fermi level which resulted in a change in both the real and imaginary part of the refractive index of the metamaterial.

FIGS. 3*a* and 3*b* illustrate schematically changes to electromagnetic radiation instant on a plasmonic metamaterial for use in some embodiments. In the detection configuration shown in FIG. 2*b* and described in relation to the tests set out above, it was determined that the reflectivity of the metamaterial sample was characterised by a strong resonant mode at a wavelength of 820 nanometres. The particular position of resonance is a function of the optical properties of each individual palladium and gold nanorod and the strong near-field interaction between them. Such an optical system exhibits a high sensitivity to changes in hydrogen concentration as a result of the physical changes which occur within the metamaterial structure on exposure to hydrogen and the corresponding complex permittivity change of, in this instance, the palladium shell of the nanostructures themselves. Both the physical change and the complex permittivity change combine to change the plasmonic properties of each individual nanostructure and modification of the palladium shell permittivity strongly modifies the optical coupling between the individual nanostructure elements forming the plasmonic metamaterial.

FIG. 3*b* illustrates a change in intensity of reflected instant light as a function of wavelength for different durations of exposure to 2% hydrogen in a nitrogen environment surrounding a test piece of metamaterial.

The hydrogen detector properties of a metamaterial, in accordance with aspects and embodiments described, are based upon pronounced optical interactions and the optical resonances which produce extraordinary changes in the reflection from the metamaterial as a result of a shift in the resonant wavelength and a change in overall extinction.

FIGS. 4*a* and 4*b* show a visual change to a sensor in the presence of hydrogen according to one embodiment. It has been found that without any special effort to maximise the response of a detector in accordance with aspects and embodiments described herein, a metamaterial structure can be configured to show a 30% change in reflection at a wavelength of 820 nanometres and a spectral shift of that resonant wavelength of approximately 30 nanometres (as shown in FIG. 3*b*). By varying the metamaterial parameters (for example, by changing nanorod dimensions, separation or thickness of the hydrogen-sensitive shell) the wavelength of operation of a metamaterial, in accordance with aspects and embodiments, can easily be tuned. As shown in FIG. 4, a sensor in accordance with aspects and embodiments described herein may be capable of displaying, in a binary manner, the presence or absence of hydrogen in an environment simply by visual inspection of a metamaterial sample. On exposure to a 2% hydrogen environment, overall reflectivity of a sample metamaterial may increase dramatically, thus allowing for a quick and simple detection mechanism for hydrogen. This may be further simplified by providing a large detector metamaterial area so that no special optical interrogation methods are required.

FIGS. 5*a* and 5*b* illustrate schematically performance of a sensor including a metamaterial such as that described in relation to FIGS. 1*a* to 1*d*. FIGS. 5*a* and 5*b* show the performance of such a sensor when exposed to different hydrogen concentrations. According to some embodiments, the sensitivity of a plasmonic metamaterial hydrogen detector is illustrated schematically by FIGS. 4*a* and 4*b*. Those Figures demonstrate the response to hydrogen in the response of a plasmonic metamaterial to hydrogen in different concentrations. At 1% concentration, the maximum change in reflectivity measured was approximately 22%. The long response time shown in FIG. 5*b* is attributed to the larger volume of the cell encapsulating the sensor (0.2 litres) in the particular test mode used. In general, the response time is known to be a function of palladium thickness, since diffusion into palladium of any hydrogen tends to act as a dominant factor in response time. Although not demonstrated by the results from the test configuration shown in FIG. 5*b*, nanorod arrays such as those described and shown in FIGS. 1*a* to 1*d* are expected to exhibit a much faster response than known hydrogen sensors.

FIG. 6*a* illustrates response to laser radiation of a plasmonic metamaterial for use in a detector according to some embodiments. It has been noticed that exposure to a relatively moderate laser fluence close to the resonant wavelength of a particular metamaterial (in this case, exposure to laser radiation at 785 nanometres, when the sample under test exhibited resonance at approximately 820 nanometres) may improve the response time of a detector in accordance with aspects and embodiments. It is believed that this is a thermal effect which is expected to produce even faster performance if the exciting laser is illuminating the hydrogen-detecting metamaterial at resonance.

A metamaterial and detector in accordance with aspects and embodiments described may offer a range of possible benefits. In particular: although a metamaterial may be constructed such that it operates outside a typical optical range of incident electromagnetic radiation, the ability to use conventional optical devices including, for example, the naked eye, to detect the presence of hydrogen may offer a particularly economical hydrogen-sensing solution. Furthermore, conventional electrical detectors may present an explosive hazard since hydrogen may be ignited if it exists in an environment in a concentration of greater than 4%.

Use of a metamaterial such as that described results in a detector which is particularly sensitive to the absorption of hydrogen. That is to say, the metamaterial structure described exhibits a particular response since each palladium-coated nanorod physically and compositionally changes its individual properties as a result of interaction with hydrogen.

It is possible to change the wavelength of operation of an optical metamaterial constructed in accordance with methods described herein, since those methods offer a wider degree of fabrication freedom and therefore wavelength of operation tuneability.

Since the system can be fabricated using an electrochemical approach comprising the steps of anodisation, electro deposition and etching, the resulting hydrogen detector is relatively cheap to manufacture and readily scalable to any size.

It will be appreciated that according to some aspects and embodiments the presence of hydrogen can easily be detected by eye, by observing the brightness or colour of a sensor or detector constructed using a plasmonic metamaterial. Detection, by eye, of a change in a sensor may result in rapid hydrogen detection and may be of importance in relation to chemical plant environments where identifying the presence or otherwise of hydrogen may be particularly important.

Furthermore, providing apparatus which includes a simple integrated source and detector arrangement can readily enable quantitative detection of hydrogen. In some embodiments, such apparatus may be converted into a wireless-based sensor and enable monitoring in remote locations.

It will be appreciated that parameters of the metamaterial forming the basis of the detector device described herein may be optimized to maximise sensitivity, wavelength operation and operating speed. Parameters of the device which may be adjusted include, for example, dimensions of the nanorods, their separation, the plasmonic material chosen for construction and the hydrogen-sensitive material chosen. Furthermore, the thickness of the hydrogen-sensitive material shell may be adjusted.

Material choices may, for example, include alternative hydrogen-sensitive materials (for example, nickel palladium composites) which may improve the speed and/or sensitivity of a palladium-based hydrogen-sensitive plasmonic metamaterial.

Further aspects and embodiments may provide a hydrogen sensor with an optical readout. It will be appreciated that some aspects and embodiments may provide a sensor which can be used as a safety device without inherent risk when exposed to high hydrogen concentrations.

It will be appreciated that hydrogen-specific sensors may be desired in a variety of commercial, domestic and academic environments. For example, fuel cell and automotive markets may require low cost hydrogen sensors. Similarly, low power sensors may be required for multiple point operations in fuel cells and in internal combustion engines. Hydrogen monitoring in power transformers is desirable. Furthermore, accurate and inexpensive hydrogen sensors immersed in oil may have considerable market potential. Further scope for deployment of aspects and embodiments described herein may exist in relation to medical diagnostic methods. Accurate hydrogen detection may be useful to determine carbohydrate breakdown deficiencies, excessive bacterial growth in the gut, lactose intolerance screening and time of passage to the small intestine.

Broadly speaking, aspects and embodiments described may provide a hydrogen detector based on an appropriate plasmonic hyperbolic metamaterial.

It will be appreciated that the apparatus and method of metamaterial enhanced detection described above and in the attached claims in relation to hydrogen detection may also be applied to detection of other materials, for example: other fluids, liquids or gases.

According to such alternative arrangements, a plasmonic metamaterial is formed or "hybridised" such that a plurality of nanostructure elements are provided comprising a plasmonic material and a target-substance sensitive material. The target-substance sensitive material may, for example, comprise an appropriately selected gas-sensitive material.

By way of example, detection of ammonia gas could be achieved in the following manner:

In one embodiment, the target substance comprises ammonia. In one embodiment, the target-substance sensitive material comprises: an appropriately selected conducting polymer. Such a conducting polymer may, for example, comprise: polypyrrole (PPy). Polypyrrole becomes sensitive to the presence of selected gases if an appropriate functional dye is incorporates within the polymer. By way of example: for the purposes of ammonia detection, incorporation of eriochrome cyanine R (ECR) in PPy shows large changes in optical spectra via a variation of the complex refractive index when exposed to ammonia in the gas phase.

Fabrication of a sensor, according to one example, may, for example, follow a chemical polymerisation route; a process that is described, for example, in Tavoli et al. (F. Tavoli and N. Alizadeh, Sensor Actuat B-Chem 176, 761 (2013)). Such a process may comprise, for example, exposing plasmonic nanostructured metamaterial elements to a solution containing both PPy and ECR to form a dye-doped polymer layer on the surface of the plasmonic nanostructure elements forming a metamaterial.

In a similar manner to the principles described in relation to hydrogen detections, the optical response of the individual plasmonic elements and the interaction between the plasmonic elements forming the metamaterial change on exposure to ammonia.

The optical scheme used to detect the presence of ammonia could then follow that described in relation to hydrogen detection.

Although illustrative embodiments of the invention have been disclosed in detail herein, with reference to the accompanying drawings, it is understood that the invention is not limited to the precise embodiment and that various changes and modifications can be effected therein by one skilled in the art without departing from the scope of the invention as defined by the appended claims and their equivalents.

The invention claimed is:

1. A plasmonic hydrogen detector, comprising:

a source of incident radiation that emits incident radiation, the incident radiation in a wavelength range, the wavelength range being 500 nanometers (nm) to 900 nm; and a sensor, the sensor including:

a structure including a support and a plurality of nanostructure elements including a plasmonic material and a separate hydrogen sensitive material that is different from the plasmonic material;

the plurality of nanostructure elements being configured on the support such that adjacent nanostructure elements are electromagnetically coupled such that, on interrogation by the incident radiation in the wavelength range, generated by the source of the incident radiation in the wavelength range, the electromagnetic field of one nanostructure element, of the plurality of nanostructure elements, spatially overlaps that of the adjacent nanostructure elements, such that the structure is a plasmonic optical metamaterial; and wherein the hydrogen sensitive material is configured to cause a change in permittivity of the plasmonic optical metamaterial in the presence of hydrogen; and a permittivity sensor operable to detect the change in permittivity of the plasmonic optical metamaterial in the presence of hydrogen.

2. The plasmonic hydrogen detector according to claim 1, wherein the plurality of nanostructure elements are configured as an array on the support.

3. The plasmonic hydrogen detector according to claim 1, wherein spacing between the adjacent nanostructure elements is a few tens of nanometres to several microns, with such spacing provided to be smaller than an effective wavelength of an intended interrogating electromagnetic radiation in the wavelength range inside the plasmonic optical metamaterial.

4. The plasmonic hydrogen detector according to claim 1, wherein the plurality of nanostructure elements are configured to provide a sub-set of nanostructure elements formed from hydrogen sensitive material interspersed amongst the plurality of nanostructure elements comprising the plasmonic material.

5. The plasmonic hydrogen detector according to claim 1, wherein each of the plurality of nanostructure elements includes the plasmonic material and the hydrogen sensitive material.

6. The plasmonic hydrogen detector according to claim 1, wherein the plurality of nanostructure elements comprise one or more of: a plasmonic material core; a plasmonic material core comprising a hollow structure; a plasmonic material core having a hydrogen sensitive material coating.

7. The plasmonic hydrogen detector according to claim 1, wherein the plurality of nanostructure elements include elongate elements extending from the support.

8. The plasmonic hydrogen detector according to claim 1, wherein the plasmonic material includes at least one of: copper, gold, silver or aluminium or a plasmonic doped semiconductor.

9. The plasmonic hydrogen detector according to claim 1, wherein the hydrogen sensitive material comprises a hydrogen absorptive material.

10. The plasmonic hydrogen detector according to claim 1, wherein the plasmonic optical metamaterial acts as a waveguide.

11. The plasmonic hydrogen detector according to claim 1, wherein the detector includes one or more of: a photo diode, a ccd, a video camera, an analogue or digital camera.

12. The plasmonic hydrogen detector according to claim 1, wherein the detector is operable to monitor intensity of reflected or transmitted radiation incident upon the sensor.

13. A method of forming a plasmonic hydrogen detector that includes a structure, of a sensor, including a support and a plurality of nanostructure elements including a plasmonic material and a separate hydrogen sensitive material that is different from the plasmonic material, the method comprising:

providing a source of incident radiation that emits incident radiation, the incident radiation in a wavelength range, the wavelength range being 500 nanometers (nm) to 900 nm;

providing the sensor; and configuring the plurality of nanostructure elements on the support such that adjacent nanostructure elements are electromagnetically coupled such that, on interrogation by the incident radiation in the wavelength range, the electromagnetic field of one nanostructure element, of the plurality of nanostructure elements, spatially overlaps that of adjacent nanostructure elements, such that the structure is a plasmonic optical metamaterial; and configuring the hydrogen sensitive material to cause a change in permittivity of the plasmonic optical metamaterial in the presence of hydrogen; and detecting the change in permittivity using a permittivity sensor, the permittivity sensor operable to detect the change in permittivity of the plasmonic optical metamaterial in the presence of hydrogen.

14. A method of detecting a change in hydrogen concentration in an environment, the method comprising:

providing the plasmonic hydrogen detector in accordance with claim 1;

arranging a source of electromagnetic radiation to be incident upon the plasmonic hydrogen detector; and monitoring the effect of the plasmonic hydrogen detector upon the incident electromagnetic radiation.

15. An apparatus operable to detect a change in hydrogen concentration in an environment, the apparatus comprising:

the plasmonic hydrogen detector in accordance with claim 1;

a source of electromagnetic radiation arranged to be incident upon the plasmonic hydrogen detector; and an electromagnetic radiation monitor operable to monitor the effect of the plasmonic hydrogen detector upon the incident electromagnetic radiation.

16. The plasmonic hydrogen detector according to claim 1, wherein the plurality of nanostructure elements are configured as an array on the support.

17. The plasmonic hydrogen detector according to claim 1, the wavelength range being 700 nanometers (nm) to 900 nm.

* * * * *